United States Patent
Berneth et al.

(10) Patent No.: US 6,726,972 B2
(45) Date of Patent: Apr. 27, 2004

(54) OPTICAL DATA STORAGE MEDIUM CONTAINING A DIAZA HEMICYANINE DYE AS THE LIGHT-ABSORBING COMPOUND IN THE INFORMATION LAYER

(75) Inventors: Horst Berneth, Leverkusen (DE); Friedrich-Karl Bruder, Krefeld (DE); Wilfried Haese, Odenthal (DE); Rainer Hagen, Leverkusen (DE); Karin Hassenrück, Düsseldorf (DE); Serguei Kostromine, Swistall (DE); Peter Landenberger, Köln (DE); Rafael Oser, Krefeld (DE); Thomas Sommermann, Bergisch Gladbach (DE); Josef-Walter Stawitz, Odenthal (DE); Thomas Bieringer, Odenthal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/102,578

(22) Filed: Mar. 20, 2002

(65) Prior Publication Data

US 2003/0071268 A1 Apr. 17, 2003

(30) Foreign Application Priority Data

| Mar. 28, 2001 | (DE) | ............................................. | 10115227 |
| Jul. 25, 2001 | (DE) | ............................................. | 10136064 |
| Dec. 21, 2001 | (EP) | ............................................. | 01130527 |
| Feb. 20, 2002 | (EP) | ............................................. | 02003812 |

(51) Int. Cl.$^7$ .............................................. B32B 3/02
(52) U.S. Cl. .................. 428/64.1; 428/64.4; 428/64.8; 430/270.16; 430/270.17
(58) Field of Search .............................. 428/64.1, 64.4, 428/64.8, 945; 430/270.14, 270.16, 270.17, 495.1, 945

(56) References Cited

U.S. PATENT DOCUMENTS

| 3,770,719 | A | 11/1973 | Fisher et al. ................. 260/158 |
| 4,039,539 | A | 8/1977 | Kühlthau ..................... 260/157 |
| 4,046,752 | A | 9/1977 | Hohmann et al. .......... 260/158 |
| 4,251,440 | A | 2/1981 | Kaeppeli ................. 260/146 R |
| 5,266,699 | A | 11/1993 | Naef et al. ..................... 546/61 |

(List continued on next page.)

FOREIGN PATENT DOCUMENTS

| EP | 0 717 081 | 6/1996 |
| EP | 0 717 402 | 6/1996 |
| EP | 0 757 083 | 2/1997 |
| EP | 1 048 701 | 11/2000 |
| GB | 2 074 597 | 11/1981 |

(List continued on next page.)

OTHER PUBLICATIONS

Patent Abstracts of Japan, vol. 1999, No. 05, May 31, 1999 & JP 11 028865 A (TDK Corp), Feb. 2, 1999–p. 2, paragraph 6—page 3, paragraph 17–p. 9, paragraph 44; table 11, —p. 10, paragraph 46; table 13.

*Primary Examiner*—Elizabeth Mulvaney
(74) *Attorney, Agent, or Firm*—Godfried R. Akorli; Diderico van Eyl

(57) ABSTRACT

An optical data storage medium containing a preferably transparent substrate which has optionally already been coated with one or more reflecting layers and onto the surface of which a photorecordable information layer, optionally one or more reflecting layers, and optionally a protective layer or an additional substrate or a top layer are applied, which data storage medium can be recorded on and read using blue or red light, preferably laser light, wherein the information layer contains a light-absorbing compound and optionally a binder, characterized in that at least one diaza hemicyanine dye is used as the light-absorbing compound.

19 Claims, 2 Drawing Sheets

U.S. PATENT DOCUMENTS

Figure 1:
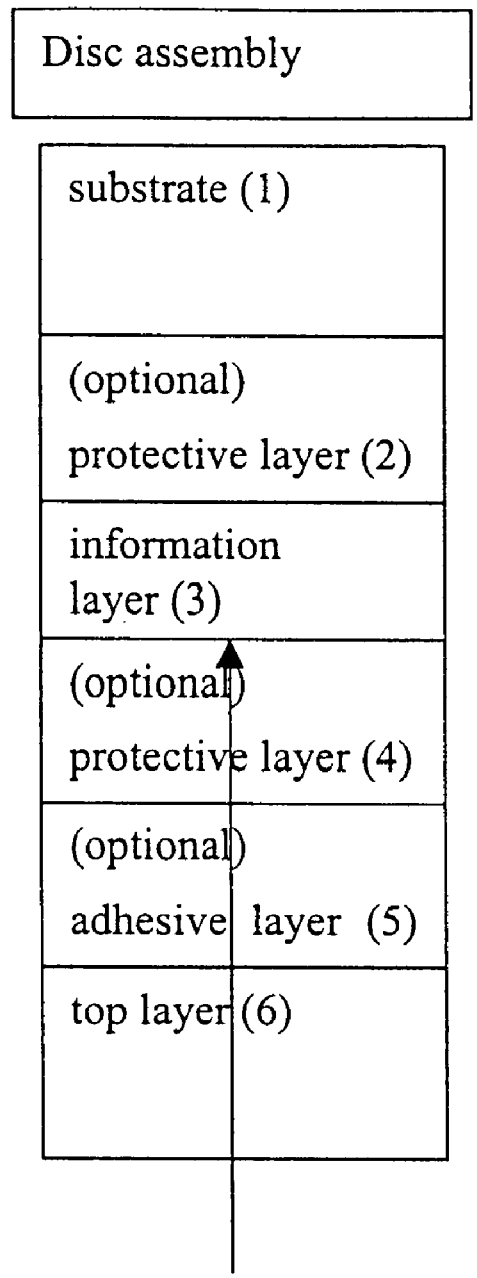

| | | | |
|---|---|---|---|
| 5,532,342 A * | 7/1996 | Ociai | 534/693 |
| 5,547,727 A * | 8/1996 | Shuttleworth | 428/64.1 |
| 5,952,475 A | 9/1999 | Berneth | 534/607 |
| 6,168,843 B1 * | 1/2001 | Kambe | 428/64.1 |
| 6,214,431 B1 | 4/2001 | Hua et al. | 428/64.1 |
| 6,214,519 B1 * | 4/2001 | Suzuki | 430/270.16 |
| 6,242,067 B1 * | 6/2001 | Kambe | 428/64.1 |
| 6,482,494 B2 * | 11/2002 | Je | 428/64.1 |

FOREIGN PATENT DOCUMENTS

| | | |
|---|---|---|
| JP | 6-336086 | 12/1994 |
| JP | 8-191171 | 7/1996 |
| JP | 25-57335 | 11/1996 |
| JP | 9-50629 | 2/1997 |
| JP | 10-58828 | 3/1998 |
| JP | 10-181206 | 7/1998 |
| JP | 11-43481 | 2/1999 |

* cited by examiner

OPTICAL DATA STORAGE MEDIUM CONTAINING A DIAZA HEMICYANINE DYE AS THE LIGHT-ABSORBING COMPOUND IN THE INFORMATION LAYER

The invention relates to a preferably once recordable optical data storage medium containing a diaza hemicyanine dye as the light-absorbing compound in the information layer, and to a process for its production.

Recordable optical data storage media using special light-absorbing substances or mixtures thereof are particularly suitable for use in high-density recordable optical data storage media which operate with blue laser diodes, and in particular GaN or SHG laser diodes (360–460 nm), and/or for use in DVD-R or CD-R discs, which operate with red (635–660 nm) or infrared (780–830 nm) laser diodes, and the application of the above-mentioned dyes to a polymer substrate, in particular polycarbonate, by spin-coating or vapour deposition.

There has recently been an enormous growth in the sales of recordable compact discs (CD-R, 780 nm), which represent the technically established system.

The next generation of optical data storage media—DVDs—is currently being introduced onto the market. By using shorter-wave laser radiation (635 to 660 nm) and a higher numerical aperture NA, the storage density can be increased. The recordable format is in this case the DVD-R.

Today, optical data storage formats which use blue laser diodes (based on GaN, JP 08191171 or Second Harmonic Generation SHG JP 09050629) (360 nm to 460 nm) with a high laser power, are being developed. Recordable optical data storage media will therefore also be used in this generation. The achievable storage density depends on the focussing of the laser spot in the information plane. The spot size is proportional to the laser wavelength λ/NA. NA is the numerical aperture of the objective lens used. The aim is to use the smallest possible wavelength λ for obtaining the highest possible storage density. Based on semiconductor laser diodes, 390 nm are presently possible.

The patent literature describes dye-based recordable optical data storage media which are equally suitable both for CD-R and DVD-R systems (JP-A 11 043 481 and JP-A 10 181 206). In order to obtain high reflectivity, a high modulation level of the readout signal and sufficient sensitivity during recording, use is made of the fact that the IR wavelength 780 nm of the CD-R is located at the base of the long-wavelength slope of the absorption peak of the dye and the red wavelength 635 nm or 650 nm of the DVD-R is located at the base of the short-wavelength slope of the absorption peak of the dye. In JP-A 02 557 335, JP-A 10 058 828, JP-A 06 336 086, JP-A 02 865 955, WO-A 09 917 284 and U.S. Pat. No. 5,266,699 this concept is extended to cover the working wavelength range of 450 nm on the short-wavelength slope and the red and IR range on the long-wavelength slope of the absorption peak.

In addition to the above-mentioned optical properties, the recordable information layer consisting of light-absorbing organic substances must have a morphology which is as amorphous as possible, in order to keep the noise signal during recording or reading as small as possible. For this purpose it is particularly preferable, when applying the substances by spin-coating from a solution or by vapour deposition and/or sublimation, to prevent crystallization of the light-absorbing substances during the subsequent top-coating with metallic or dielectric layers in vacuo.

The amorphous layer of light-absorbing substances should preferably have high thermal stability, since otherwise additional layers of organic or inorganic material applied by sputtering or vapour deposition onto the light-absorbing information layer form blurred boundaries due to diffusion and thus have an adverse effect on the reflectivity.

In addition, if a light-absorbing substance has inadequate thermal stability at the boundary to a polymeric substrate, it can diffuse into the latter and again have an adverse effect on the reflectivity.

If the light-absorbing substance has too high a vapour pressure, it can sublime during the above-mentioned sputtering or vapour deposition of additional layers in a high vacuum and thus reduce the desired layer thickness. This in turn has a negative effect on reflectivity.

The object of the invention is therefore to provide suitable compounds which meet the high demands (such as light stability, a favourable signal-to-noise ratio, damage-free application to the substrate material, etc.) for use in the information layer of a recordable optical data storage medium, in particular for high-density recordable optical data storage formats in a laser wavelength range of 340 to 680 nm.

Surprisingly, it has been found that light-absorbing compounds from the diaza hemicyanine group of dyes are particularly suitable for satisfying the above-mentioned requirement profile.

The invention therefore relates to an optical data storage medium containing a preferably transparent substrate which has optionally already been coated with one or more reflecting layers and onto the surface of which a photorecordable information layer, optionally one or more reflecting layers and optionally a protective layer or an additional substrate or a top layer are applied, which data storage medium can be recorded on and read using blue or red light, preferably laser light, wherein the information layer contains a light-absorbing compound and optionally a binder, characterized in that at least one diaza hemicyanine dye is used as the light-absorbing compound.

Blue laser light is particularly preferred.

The light-absorbing compound should preferably be thermally modifiable. Preferably the thermal modification is carried out at a temperature of <600° C., particularly preferably at a temperature of <400° C., very particularly preferably at a temperature of <300° C., and in particular at a temperature of <200° C. Such a modification can for example be the decomposition or chemical modification of the chromophoric centre of the light-absorbing compound.

A diaza hemicyanine of the formula (I) is preferred

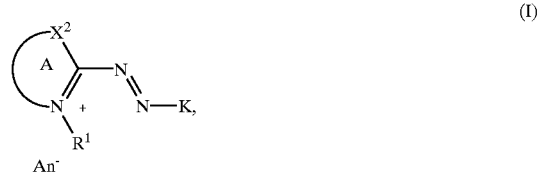

in which

K represents a radical of the formulae (II) to (IV)

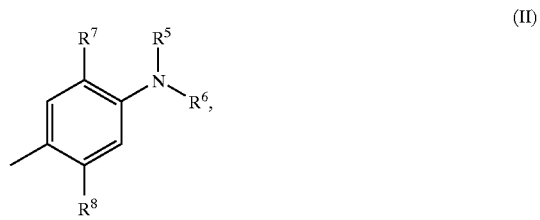

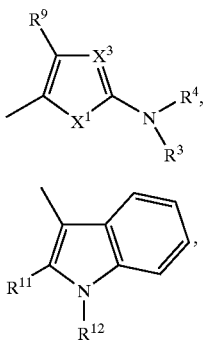

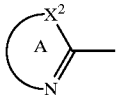

$X^1$ represents O or S, $X^2$ represents O, S, CH or N—$R^2$, $X^3$ represents N, CH or C—CN, $R^1$, $R^2$ and $R^{12}$ independently of one another represent $C_1$- to $C_{16}$-alkyl, $C_3$- to $C_6$-alkenyl, $C_5$- to $C_7$-cycloalkyl or $C_7$- to $C_{16}$-aralkyl, A together with $X^2$ and the C-atom bound therebetween represents a five-membered aromatic or quasi-aromatic heterocyclic ring which can contain 1 to 4 hetero atoms and/or can be benzo- or naphtho-fused and/or substituted by non-ionic radicals, $R^3$, $R^4$, $R^5$ and $R^6$ independently of one another represent hydrogen, $C_1$- to $C_{16}$-alkyl, $C_4$- to $C_7$-cycloalkyl, $C_7$- to $C_{16}$-aralkyl or a heterocyclic radical or $NR^3R^4$ or $NR^5R^6$ independently of one another represent a five- or six-membered saturated ring which is attached via N and can additionally contain an N or O atom and/or be substituted by non-ionic radicals, $R^7$ represents hydrogen, $C_1$- to $C_{16}$-alkyl, $C_1$- to $C_{16}$-alkoxy or halogen or $R^7$ and $R^5$ form a two- or three-membered bridge which can contain an O or N atom and/or be substituted by non-ionic radicals, $R^8$ represents hydrogen, $C_1$- to $C_{16}$-alkyl, $C_1$- to $C_{16}$-alkoxy, halogen, cyano, $C_1$- to $C_4$-alkoxycarbonyl, O—CO—$R^{10}$, NH—CO—$R^{10}$, O—$SO_2$—$R^{10}$ or NH—$SO_2$—$R^{10}$, $R^9$ represents hydrogen, $C_1$- to $C_4$-alkyl or $C_6$- to $C_{10}$-aryl, $R^{10}$ represents hydrogen, $C_1$- to $C_{16}$-alkyl, $C_4$- to $C_7$-cycloalkyl, $C_7$- to $C_{16}$-aralkyl, $C_1$- to $C_{16}$-alkoxy, mono- or bis-$C_1$- to $C_{16}$-alkylamino, $C_6$- to $C_{10}$-aryl, $C_6$- to $C_{10}$-aryloxy, $C_6$- to $C_{10}$-arylamino or a heterocyclic radical, $R^{11}$ represents hydrogen, $C_1$- to $C_4$-alkyl or $C_6$- to $C_{10}$-aryl and $An^-$ represents an anion.

Suitable non-ionic radicals are for example $C_1$- to $C_4$-alkyl, $C_1$- to $C_4$-alkoxy, halogen, cyano, nitro, $C_1$- to $C_4$-alkoxycarbonyl, $C_1$- to $C_4$-alkylthio, $C_1$- to $C_4$-alkanoylanino, benzoylamino, mono- or di-$C_1$- to $C_4$-alkylamino.

Alkyl, alkoxy, aryl and heterocyclic radicals can optionally contain additional radicals such as alkyl, halogen, nitro, cyano, CO—$NH_2$, alkoxy, trialkylsilyl, trialkyl-siloxy or phenyl, the alkyl and alkoxy radicals can be straight-chain or branched, the alkyl radicals can be partially halogenated or perhalogenated, the alkyl and alkoxy radicals can be ethoxylated or propoxylated or silylated, adjacent alkyl and/or alkoxy radicals on aryl or heterocyclic radicals can together form a three- or four-membered bridge and the heterocyclic radicals can be benzo-fused and/or quaternized.

The ring A of the formula

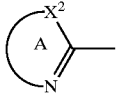

particularly preferably represents thiazol-2-yl, benzothiazol-2-yl, benzoxazol-2-yl, benzimidazol-2-yl, imidazol-2-yl, pyrazol-3-yl, 1,3,4-triazol-2-yl, 1,3,4-thiadiazol-2-yl, 1,2,4-thiadiazol-5-yl, 2- or 4-pyridyl or 2- or 4-quinolyl, wherein the aforementioned rings can each be substituted by $C_1$- to $C_6$-alkyl, $C_1$- to $C_6$-alkoxy, fluorine, chlorine, bromine, iodine, cyano, nitro, $C_1$- to $C_6$-alkoxycarbonyl, $C_1$- to $C_6$-alkylthio, $C_1$- to $C_6$-acylamino, $C_6$- to $C_{10}$-aryl, $C_6$- to $C_{10}$-aryloxy, $C_6$- to $C_{10}$-arylcarbonylamino, mono- or di-$C_1$- to $C_6$-alkylamino, N—$C_1$- to $C_6$-alkyl-N—$C_6$- to $C_{10}$-arylamino, pyrrolidino, morpholino or piperazino.

In a particularly preferred form the diaza hemicyanines used are those of the formula (I), in which the ring A of the formula

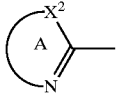

represents thiazol-2-yl, benzothiazol-2-yl, wherein $X^2$ represents S and the aforementioned radicals can each be substituted by methyl, ethyl, methoxy, ethoxy, chlorine, cyano, methoxycarbonyl or ethoxycarbonyl, or represents 1,3,4-triazolyl or 1,3,4-thiadiazolyl, wherein $X^2$ represents N—$R^2$ or S, respectively, and the aforementioned radicals can each be substituted by methyl, ethyl, phenyl, methoxy, ethoxy, methylthio, ethylthio, amino, anilino, dimethylamino, diethylamino, dipropylamino, dibutylamino, N-methyl-N-cyanethylamino, N-methyl-N-hydroxy-ethylamino, N-methyl-N-phenylamino, di-(cyanethyl)amino, di-(hydroxyethyl)amino, cyanethylamino, hydroxyethylamino, pyrrolidino, piperidino, morpholino or a radical of the formula

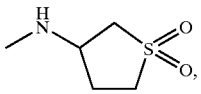

K represents a radical of the formulae (II), (III) or (IV), $X^1$ represents O or S, $X^3$ represents N, CH or C—CN, $R^1$, $R^2$ and $R^{12}$ independently of one another represent methyl, ethyl, propyl, butyl, pentyl, hexyl, benzyl, phenethyl, phenylpropyl, allyl, cyclohexyl, chloroethyl, cyanomethyl, cyanoethyl, cyanopropyl, hydroxyethyl, 2-hydroxypropyl, methoxyethyl or ethoxyethyl, $R^3$, $R^4$, $R^5$ and $R^6$ independently of one another represent methyl, ethyl, propyl, butyl, pentyl, hexyl, benzyl, phenethyl, phenylpropyl, cyclohexyl, chloroethyl, cyanomethyl, cyanoethyl, cyanopropyl, hydroxyethyl, 2-hydroxypropyl, methoxyethyl, ethoxyethyl, methoxycarbonylethyl, ethoxycarbonylethyl, acetoxyethyl, propionyloxyethyl or a radical of the formula

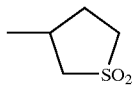

and $R^3$ and $R^5$ can additionally represent hydrogen or $NR^3R^4$ and $NR^5R^6$ independently of one another represent pyrrolidino, piperidino, N-methylpiperazino, N-ethylpiperazino, N-hydroxyethylpiperazino or morpholino, $R^7$ represents hydrogen, methyl, methoxy or chlorine or $R^7$; $R^5$ represent a —(CH$_2$)$_2$—, —(CH$_2$)$_3$—, —C(CH$_3$)—CH$_2$—C(CH$_3$)$_2$— or —O—(CH$_2$)$_2$— bridge, $R^8$ represents hydrogen, methyl, methoxy or chlorine, $R^9$ represents hydrogen, $R^{11}$ represents hydrogen, methyl or phenyl and An$^-$ represents an anion.

Suitable anions An$^-$ are all monovalent anions or one equivalent of a polyvalent anion. Preferably the anions are colourless. Suitable anions are, for example, chloride, bromide, iodide, tetrafluoroborate, perchlorate, hexafluorosilicate, hexafluorophosphate, methosulphate, ethosulphat, C$_1$- to C$_{10}$-alkanesulphonate, C$_1$- to C$_{10}$-perfluoroalkane sulphonate, C$_1$- to C$_{10}$-alkanoate optionally substituted by chlorine, hydroxyl or C$_1$- to C$_4$ alkoxy, benzene sulphonate, naphthalene sulphonate or biphenyl sulphonate optionally substituted by nitro, cyano, hydroxyl, C$_1$- to C$_{25}$-alkyl, perfluoro-C$_1$- to C$_4$-alkyl, C$_1$- to C$_4$-alkoxycarbonyl or chlorine, benzene disulphonate, naphthalene disulphonate or biphenyl disulphonate optionally substituted by nitro, cyano, hydroxyl, C$_1$- to C$_4$-alkyl, C$_1$- to C$_4$-alkoxy, C$_1$- to C$_4$-alkoxycarbonyl or chlorine, benzoate optionally substituted by nitro, cyano, C$_1$- to C$_4$-alkyl, C$_1$- to C$_4$-alkoxy, C$_1$- to C$_4$-alkoxycarbonyl, benzoyl, chlorobenzoyl or toluoyl, the anion of naphthalenedicarboxylic acid, diphenyl ether disulphonate, tetraphenyl borate, cyanotriphenyl borate, tetra-C$_1$- to C$_{20}$-alkoxyborate, tetraphenoxyborate, 7,8- or 7,9-dicarba-nido-undecaborate (1-) or (2-), which are optionally substituted on the B- and/or C-atoms by one or two C$_1$- to C$_{12}$-alkyl or phenyl groups, dodecahydro-dicarbadodecaborate(2-) or B—C$_1$- to C$_{12}$-alkyl-C-phenyl-dodecahydro-dicarbadodecaborate(1-).

Bromide, iodide, tetrafluoroborate, perchlorate, methane sulphonate, benzene sulphonate, toluene sulphonate, dodecylbenzene sulphonate and tetradecane sulphonate are preferred.

In a very particularly preferred form the diaza hemicyanines used are those of the formulae (VI) to (IX)

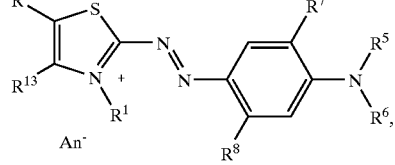

(VI)

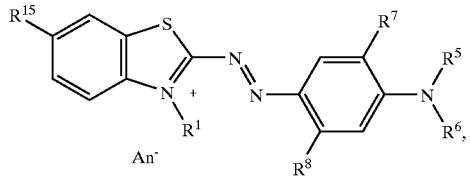

(VII)

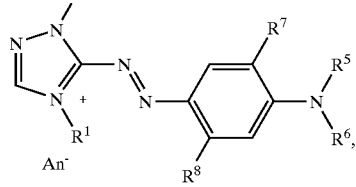

(VIII)

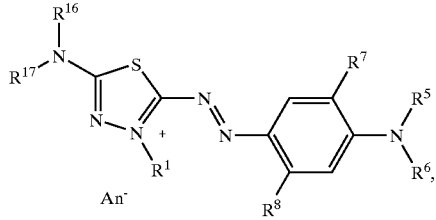

(IX)

in which $R^1$ and $R^2$ independently of one another represent methyl, ethyl, propyl, butyl, pentyl, hexyl, benzyl, cyclohexyl, chloroethyl, cyanomethyl, cyanoethyl, hydroxyethyl, 2-hydroxypropyl, methoxyethyl, ethoxyethyl or a radical of the formula

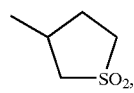

$R^5$ and $R^6$ independently of one another represent methyl, ethyl, propyl, butyl, pentyl, hexyl, benzyl, cyclohexyl, chloroethyl, cyanoethyl, hydroxyethyl, 2-hydroxypropyl, methoxyethyl, ethoxyethyl, methoxycarbonylethyl, ethoxycarbonylethyl or acetoxyethyl or $NR^5R^6$ represents pyrrolidino, piperidino or morpholino, $R^7$ represents hydrogen or $R^7$; $R^5$ represent a —(CH$_2$)$_2$—, —C(CH$_3$)—CH$_2$—C(CH$_3$)$_2$— or —O—(CH$_2$)$_2$— bridge, $R^8$ represents hydrogen, $R^{13}$, $R^{14}$ and $R^{15}$ independently of one another represent hydrogen, methyl, methoxy, chloro, nitro or cyano, $R^{16}$ and $R^{17}$ independently of one another represent methyl, ethyl, propyl, butyl, pentyl, hexyl, benzyl, cyclohexyl, chloroethyl, cyanoethyl, hydroxyethyl, 2-hydroxypropyl, methoxyethyl, ethoxyethyl, methoxycarbonylethyl, ethoxycarbonylethyl, acetoxyethyl or phenyl and $R^{16}$ additionally represents hydrogen or $NR^{16}R^{17}$ represents pyrrolidino, piperidino or morpholino, and An$^-$ represents tetrafluoroborate, perchlorate, hexafluorosilicate, hexafluorophosphate, iodide, rhodanide, cyanate, hydroxy acetate, methoxy acetate, lactate, citrate, methane sulphonate, ethane sulphonate, benzene sulphonate, toluene sulphonate, butylbenzene sulphonate, chlorobenzene sulphonate, dodecylbenzene sulphonate or naphthalene sulphonate, wherein all alkyl radicals can be branched.

In a very particularly preferred form the diaza hemicyanines used are those of the formulae (X) to (XIII)

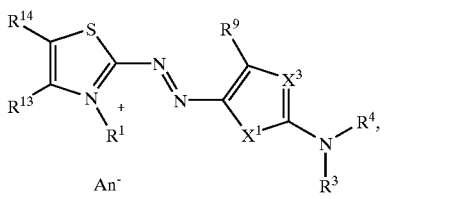

(X)

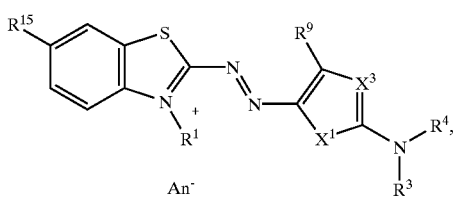

(XI)

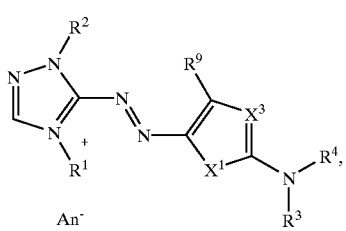

(XII)

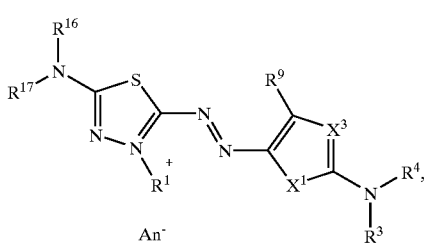

(XIII)

in which $R^1$ and $R^2$ independently of one another represent methyl, ethyl, propyl, butyl, pentyl, hexyl, benzyl, cyclohexyl, chloroethyl, cyanomethyl, cyanoethyl, hydroxyethyl, 2-hydroxypropyl, methoxyethyl, ethoxyethyl or a radical of the formula

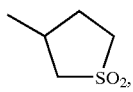

$X^1$ represents O and
$X^3$ represents CH or
$X^1$ represents S and
$X^3$ represents N, CH or C—CN, $R^3$ and $R^4$ independently of one another represent methyl, ethyl, propyl, butyl, pentyl, hexyl, benzyl, cyclohexyl, chloroethyl, cyanoethyl, hydroxyethyl, 2-hydroxypropyl, methoxyethyl, ethoxyethyl, methoxycarbonylethyl, ethoxycarbonylethyl or acetoxyethyl or $NR^3R^4$ represents pyrrolidino, piperidino or morpholino, $R^9$ represents hydrogen, $R^{13}$, $R^{14}$ and $R^{15}$ independently of one another represent hydrogen, methyl, methoxy, chloro, nitro or cyano, $R^{16}$ and $R^{17}$ independently of one another represent methyl, ethyl, propyl, butyl, pentyl, hexyl, benzyl, cyclohexyl, chloroethyl, cyanoethyl, hydroxyethyl, 2-hydroxypropyl, methoxyethyl, ethoxyethyl, methoxycarbonylethyl, ethoxycarbonylethyl, acetoxyethyl or phenyl and $R^{16}$ additionally represents hydrogen or $NR^{16}R^{17}$ represents pyrrolidino, piperidino or morpholino, and $An^-$ represents tetrafluoroborate, perchlorate, hexafluorosilicate, hexafluorophosphate, iodide, rhodanide, cyanate, hydroxy acetate, methoxy acetate, lactate, citrate, methane sulphonate, ethane sulphonate, benzene sulphonate, toluene sulphonate, butylbenzene sulphonate, chlorobenzene sulphonate, dodecylbenzene sulphonate or naphthalene sulphonate, wherein all alkyl radicals can be branched.

In a very particularly preferred form the diaza hemicyanines used are those of the formulae (XIV) to (XVII)

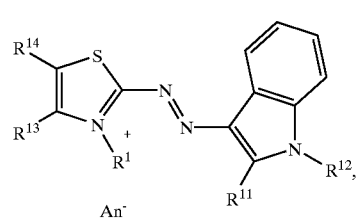

(XIV)

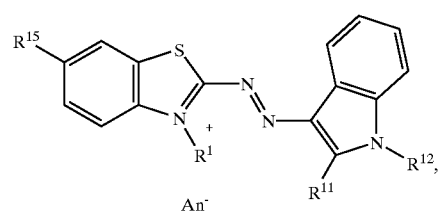

(XV)

(XVI)

(XVII)

in which $R^1$, $R^2$ and $R^{12}$ independently of one another represent methyl, ethyl, propyl, butyl, pentyl, hexyl, benzyl, cyclohexyl, chloroethyl, cyanomethyl, cyanoethyl, hydroxyethyl, 2-hydroxypropyl, methoxyethyl, ethoxyethyl or a radical of the formula

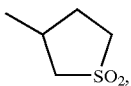

$R^{13}$, $R^{14}$ and $R^{15}$ independently of one another represent hydrogen, methyl, methoxy, chloro, nitro or cyano, $R^{16}$ and $R^{17}$ independently of one another represent methyl, ethyl, propyl, butyl, pentyl, hexyl, benzyl, cyclohexyl, chloroethyl, cyanoethyl, hydroxyethyl, 2-hydroxypropyl, methoxyethyl, ethoxyethyl, methoxycarbonylethyl, ethoxycarbonylethyl, acetoxyethyl or phenyl and $R^{16}$ additionally represents hydrogen or $NR^{16}R^{17}$ represents pyrrolidino, piperidino or morpholino, $R^{11}$ represents hydrogen, methyl or phenyl and $An^-$ represents tetrafluoroborate, perchlorate, hexafluorosilicate, hexafluorophosphate, iodide, rhodanide, cyanate, hydroxy acetate, methoxy acetate, lactate, citrate, methane sulphonate, ethane sulphonate, benzene sulphonate, toluene sulphonate, butylbenzene sulphonate, chlorobenzene sulphonate, dodecylbenzene sulphonate or naphthalene sulphonate, wherein all alkyl radicals can be branched.

In a very particularly preferred form the diaza hemicyanines used are those of the formulae (IX), (XIII) and (XVII).

For a recordable optical data storage medium according to the invention which is recorded on and read using light from a blue laser, such diaza hemicyanine dyes are preferred whose absorption maximum $\lambda_{max2}$ is in the range from 420 to 550 nm, wherein the wavelength $\lambda_{1/2}$ at which the extinction on the short-wavelength slope of the absorption maximum of the wavelength $\lambda_{max2}$ is half the extinction value at $\lambda_{max2}$, and the wavelength $\lambda_{1/10}$, at which the extinction on the short-wavelength slope of the absorption maximum of the wavelength $\lambda_{max2}$ is a tenth of the extinction value at $\lambda_{max2}$, are preferably in each case no further than 50 nm away from each other. Preferably such a diaza hemicyanine dye does not display a shorter-wave maximum $\lambda_{max1}$ at a wavelength below 350 nm, particularly preferably below 320 nm, and very particularly preferably below 290 nm.

Preferred diaza hemicyanine dyes are those with an absorption maximum $\lambda_{max2}$ of 410 to 530 nm.

Particularly preferred diaza hemicyanine dyes are those with an absorption maximum $\lambda_{max2}$ of 420 to 510 nm.

Very particularly preferred diaza hemicyanine dyes are those with an absorption maximum $\lambda_{max2}$ of 430 to 500 nm.

In these diaza hemicyanine dyes $\lambda_{1/2}$ and $\lambda_{1/10}$, as defined above, are preferably no further than 40 nm, particularly preferably no further than 30 nm, and very particularly preferably no further than 20 nm away from each other.

For a recordable optical data storage medium according to the invention which is recorded on and read using light from a red laser, such diaza hemicyanine dyes are preferred whose absorption maximum $\lambda_{max2}$ is in the range from 500 to 650 nm, wherein the wavelength $\lambda_{1/2}$ at which the extinction on the long-wavelength slope of the absorption maximum of the wavelength $\lambda_{max2}$ is half the extinction value at $\lambda_{max2}$, and the wavelength $\lambda_{1/10}$, at which the extinction on the long-wavelength slope of the absorption maximum of the wavelength $\lambda_{max2}$ is a tenth of the extinction value at $\lambda_{max2}$, are preferably in each case no further than 50 nm away from each other. Preferably such a diaza hemicyanine dye does not display a longer-wave maximum $\lambda_{max}$ at a wavelength below 750 nm, particularly preferably below 800 nm, and very particularly preferably below 850 nm.

Preferred diaza hemicyanine dyes are those with an absorption maximum $\lambda_{max2}$ of 530 to 630 nm.

Particularly preferred diaza hemicyanine dyes are those with an absorption maximum $\lambda_{max2}$ of 550 to 620 nm.

Very particularly preferred diaza hemicyanine dyes are those with an absorption maximum $\lambda_{max2}$ of 580 to 610 nm.

In these diaza hemicyanine dyes $\lambda_{1/2}$ and $\lambda_{1/10}$, as defined above, are preferably no further than 40 nm, particularly preferably no further than 30 nm, and very particularly preferably no further than 20 nm away from each other.

At the absorption maximum $\lambda_{max2}$ the diaza hemicyanine dyes have a molar extinction coefficient $\epsilon$ of >30000 l/mol cm, preferably >40000 l/mol cm, particularly preferably >50000 l/mol cm and very particularly preferably >70000 l/mol cm.

The absorption spectra are, for example, measured in solution.

Suitable diaza hemicyanines having the required spectral properties are in particular those in which the change in the dipole moment $\Delta\mu = |\mu_g - \mu_{ag}|$, i.e. the positive difference between the dipole moments in the ground state and the first excited state is as small as possible, i.e. preferably <5 D, and particularly preferably <2 D. A method of determining such a change in the dipole moment $\Delta\mu$ is described, for example, in F. Würthner et al., Angew. Chem. 1997, 109, 2933 and in the literature cited therein. Low solvatochromism (methanol/methylene chloride) is also a suitable criterion for selection. Preferred diaza hemicyanines are those whose solvatochromism $\Delta\lambda = |\lambda_{methylene\ chloride} - \lambda_{methanol}|$, i.e. the positive difference between the absorption wavelengths in the solvents methylene chloride and methanol, is <25 nm, particularly preferably <15 nm, and very particularly preferably <5 nm.

Diaza hemicyanines of the formulae (I) and (VI) to (XVII) are known, for example, from BE 825 455, DE-OS 1 044 023, DE-OS 2 811 258, DE-OS 1 163 775.

Another part of the invention are diaza hemicyanines of formula (I), wherein K means a radical of formula (III) and the other residues have the above meaning. Another special part of the invention are diaza hemicyanines of the formulae (X), (XI), (XII) or (XIII), wherein the residues have the above meaning.

The light-absorbing substances described guarantee sufficiently high reflectivity (>10%) of the optical data storage medium in the unrecorded state and sufficiently high absorption for the thermal degradation of the information layer upon spotwise illumination with focussed light, if the wavelength of the light is in the range from 360 to 460 nm and 600 to 680 nm. The contrast between the recorded and unrecorded areas of the data storage medium is effected by the change in reflectivity in terms of the amplitude as well as the phase of the incident light as a result of the changed optical properties of the information layer following thermal degradation.

The diaza hemicyanine dyes are preferably applied to the optical data storage medium by spin-coating or vacuum coating. The diaza hemicyanines can be mixed with other dioaza hemicyanines or with other dyes having similar spectral properties. The information layer can contain additives in addition to the diaza hemicyanine dyes, such as binders, wetting agents, stabilizers, diluents and sensitizers as well as other constituents.

In addition to the information layer, the optical data storage medium can contain other layers such as metal layers, dielectric layers and protective layers. Metals and dielectric layers are used, for example, for adjusting the reflectivity and the thermal balance. Depending on the laser wavelength, the metals can be gold, silver or aluminium, etc. Dielectric layers are, for example, silicon dioxide and silicon nitride. Protective layers are, for example, photocurable surface coatings, adhesive layers and protective films.

Adhesive layers can consist of a pressure-sensitive material.

Pressure-sensitive adhesive layers consist mainly of acrylic adhesives. Nitto Denko DA-8320 or DA-8310, which are disclosed in the patent JP-A 11-273147, can, for example, be used for this purpose.

The optical data storage medium has, for example, the following layer assembly (cf. FIG. 1): a transparent substrate (1), optionally a protective layer (2), an information layer (3), optionally a protective layer (4), optionally an adhesive layer (5) and a top layer (6).

Preferably, the optical data storage medium assembly can contain:

a preferably transparent substrate (1), onto whose surface at least one photorecordable information layer (3), which can be recorded on using light, preferably laser light, optionally a protective layer (4), optionally an adhesive layer (5) and a transparent top layer (6) are applied;

a preferably transparent substrate (1), onto whose surface a protective layer (2), at least one information layer (3) which can be recorded on using light, preferably laser light, optionally an adhesive layer (5) and a transparent top layer (6) are applied;

a preferably transparent substrate (1), onto whose surface optionally a protective layer (2), at least one information layer (3) which can be recorded on using light, preferably laser light, optionally a protective layer (4), optionally an adhesive layer (5) and a transparent top layer (6) are applied;

a preferably transparent substrate (1), onto whose surface at least one information layer (3) which can be recorded on using light, preferably laser light, optionally an adhesive layer (5) and a transparent top layer (6) are applied.

Figure 2:
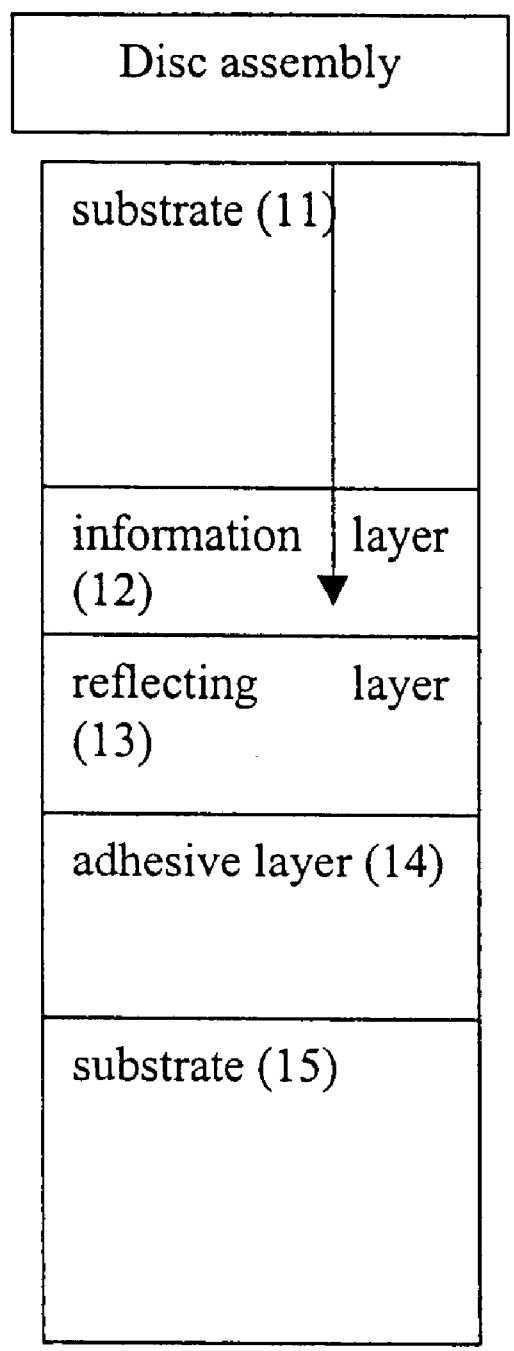

Alternatively, the optical data storage medium has for example the following layer assembly (cf. FIG. 2): a preferably transparent substrate (11), an information layer (12), optionally a reflecting layer (13), optionally an adhesive layer (14) and an additional, preferably transparent, substrate (15).

The invention also relates to optical data storage media according to the invention which are recorded on using blue or red light, in particular laser light.

The following examples illustrate the subject matter of the invention:

EXAMPLES

Example 1

4 g of 2-amino-5-(diisopropylamino)-1,3,4-thiadiazole were dissolved in 40 ml of glacial acetic acid. 8 ml of 85% by weight phosphoric acid and 6 ml of 48% by weight sulphuric acid were added dropwise at 10° C. 6.8 g of nitrosylsulphuric acid (40% by weight in sulphuric acid) were then added dropwise at 5° C. over a period of 30 mins. After 4 h at 0–5° C. the nitrite excess was destroyed with amidosulphonic acid.

This diazotized product was added dropwise at 10° C. over a period of 1 hour to a solution of 5 g of 2-morpholino-4-phenylthiazole in 30 ml of glacial acetic acid, a pH of 3 being maintained with a 20% by weight aqueous soda solution. After stirring overnight at a pH of 3.5 the mixture was filtered off with suction and the residue was washed with water. The solid was stirred into 100 ml of water and the mixture was adjusted to a pH of 7.5, filtered off with suction once again and the residue was washed with water. After drying, the crude product was dissolved in 100 ml of toluene. By slowly adding 400 ml of hexane with stirring, the product was precipitated, filtered off with suction, washed with hexane and afterwards with water and dried. 3.7 g (41% of theory) of a violet powder of the formula

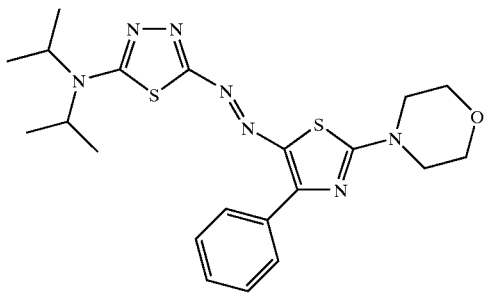

was obtained.

M.p.=155° C.

$\lambda_{max}$(dioxane)=531 nm.

2.3 g of the above azo dye were dissolved in 20 ml of glacial acetic acid. 1.3 g of dimethyl sulfate were added and the mixture was stirred at 70° C. for 5 hours. After cooling to room temperature 200 ml of water were added. The solution was extracted with 50 ml of toluene and afterwords with 100 ml of chloroform. The chloroform phase was evaporated to dryness. The resulting violet dye was solved in 30 ml of methanol. 0.6 g of lithium perchlorate were added. After stirring over night the precipitated product was filtered off with suction, washed with methanol and dried. 1.5 g (53% of theory) of a violet powder of the formula

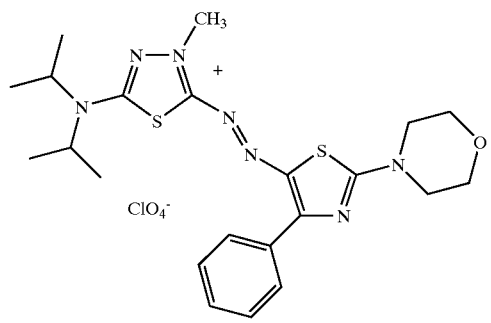

was obtained.

$\lambda_{max}$(methanol)=592 nm $\epsilon$=30100 l/mol cm

Solubility: >2% in TFP (2,2,3,3-tetrafluoropropanol)

a glassy film

Diaza hemicyanine dyes which are also suitable are listed in the table:

| Ex. | [structure with A-N+-R1, X2] | K | An− | $\lambda_{max}$ /nm[1] | $\epsilon$ /l/mol cm | $\lambda_{1/2}$-$\lambda_{1/10}$ /nm | $\Delta\lambda$[2] /nm |
|---|---|---|---|---|---|---|---|
| 2 | tetrahydrothiophene-1,1-dioxide-NH-thiadiazolium (dimethyl) | 1-methyl-2-phenyl-3-methylindole | CH₃OSO₃⁻ | 508 | 36570 | | |
| 3 | " | 4-(4-methylphenyl)morpholine | ClO₄⁻ | 602 | 79750 | 21[4] | |
| 4 | (dimethylamino)-dimethyl-thiadiazolium | 5-methyl-2-(dimethylamino)thiazole | ClO₄⁻ | 580 | 56200 | | |
| 5 | (diisopropylamino)-dimethyl-thiadiazolium | " | ClO₄⁻ | 582 | 56800 | | |
| 6 | " | 5-methyl-2-(dimethylamino)furan | ClO₄⁻ | 610 | | | |
| 7 | " | 4-isopropyl-5-methyl-2-(dimethylamino)-3-cyanothiophene | ClO₄⁻ | 588 | | | |
| 8 | " | N,N-diethyl-2-methyl-5-(methylsulfonamido)aniline | BF₄⁻ | 590 | 47900 | | |
| 9 | " | 2-methoxy-4-methyl-N-(1,1-dioxo-tetrahydrothiophen-3-yl)aniline | BF₄⁻ | 590 | 52100 | | |

-continued
| Ex. | 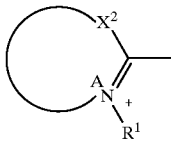 | K | An⁻ | $\lambda_{max}$ /nm[1] | $\epsilon$ /l/mol cm | $\lambda_{1/2}$-$\lambda_{1/10}$ /nm | $\Delta\lambda$[2] /nm |
|---|---|---|---|---|---|---|---|
| 10 | " | 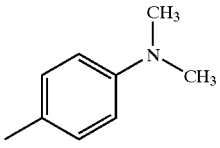 | BF₄⁻ | 600 | 56010 | 24[4] | |
| 11 | " | 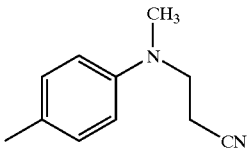 | BF₄⁻ | 589 | 56680 | | |
| 12 | " | 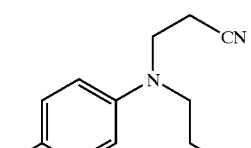 | BF₄⁻ | 568 | | | |
| 13 | 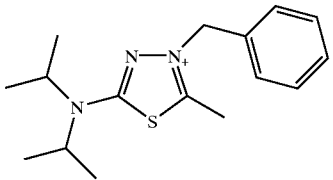 | " | ClO₄⁻ | 583 | 60260 | | |
| 14 | 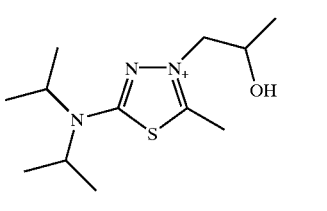 | 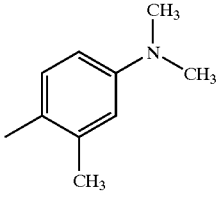 | ClO₄⁻ | 602 | 59430 | | |
| 15 | 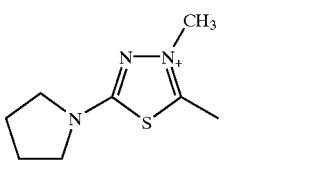 | " | ClO₄⁻ | 599 | 67110 | 23[4] | |
| 16 | " | 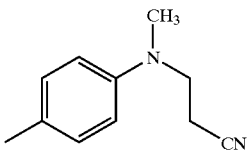 | ClO₄⁻ | 587 | 82300 | | 10 |
| 17 | 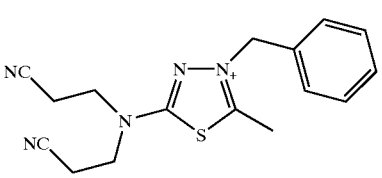 | " | ClO₄⁻ | 606 | 74560 | 23[4] | |

-continued

| Ex. | (structure with X², A, N+, R¹) | K | An⁻ | $\lambda_{max}$ /nm[1] | $\epsilon$ /l/mol cm | $\lambda_{1/2}$-$\lambda_{1/10}$ /nm | $\Delta\lambda$[2] /nm |
|---|---|---|---|---|---|---|---|
| 18 | NC-CH₂CH₂-N(CH₃)-(2-amino-3-methyl-5-methyl-1,3,4-thiadiazolium) | 4-methyl-N,N-diethylaniline | ClO₄⁻ | 606 | 77260 | 21[4] | |
| 19 | " | 2-methoxy-4-methyl-N-cyclohexylaniline | PF₆⁻ | 592 | 77300 | | |
| 20 | " | 4-methyl-N-(2-cyanoethyl)aniline | BF₄⁻ | 587 | 72570 | | |
| 21 | NC-CH₂CH₂-N(cyclohexyl)-(2-amino-3-methyl-5-methyl-1,3,4-thiadiazolium) | 4-methyl-N-methyl-N-benzylaniline | BF₄⁻ | 601 | 82610 | | |
| 22 | HO-CH(CH₃)CH₂-N[CH₂CH(OH)CH₃]-(2-amino-3-methyl-5-methyl-1,3,4-thiadiazolium) | " | PF₆⁻ | 599 | 56320 | | |
| 23 | morpholino-(2-amino-3-methyl-5-methyl-1,3,4-thiadiazolium) | 4-methyl-N,N-dimethylaniline | BF₄⁻ | 597 | 63100 | | |
| 24 | morpholino-(2-amino-3-benzyl-5-methyl-1,3,4-thiadiazolium) | 4-methyl-N-morpholinoaniline | BF₄⁻ | 597 | 76600 | | 12 |

-continued
| Ex. | 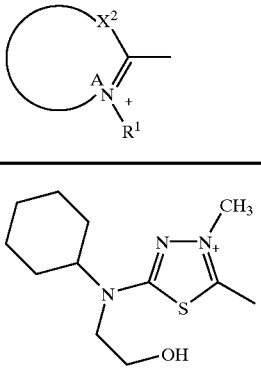 | K | An⁻ | $\lambda_{max}$ /nm[1] | ε /l/mol cm | $\lambda_{1/2}$-$\lambda_{1/10}$ /nm | Δλ[2] /nm |
|---|---|---|---|---|---|---|---|
| 25 | 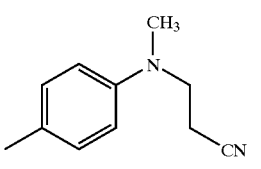 | 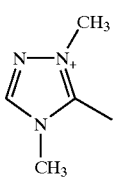 | ClO₄⁻ | 588 | 54700 | | |
| 26 | 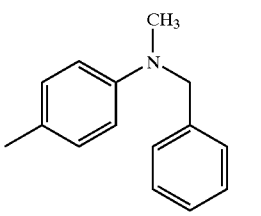 | 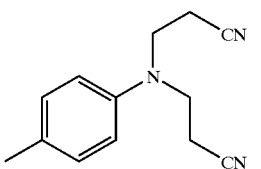 | BF₄⁻ | 526 | 53970 | 42[3] 18[4] | |
| 27 | " | 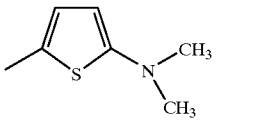 | ClO₄⁻ | 492 | 52100 | | |
| 28 | " | 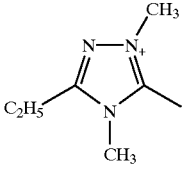 | Br⁻ | 460 | | | |
| 29 | 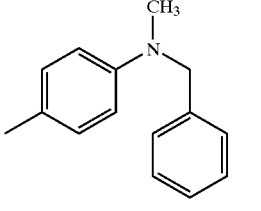 | 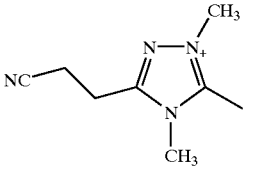 | ClO₄⁻ | 538 | | | |
| 30 | 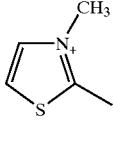 | " | ClO₄⁻ | 534 | | | |
| 31 | 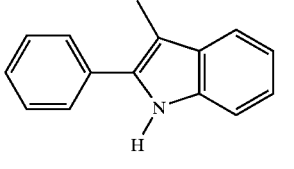 | | ClO₄⁻ | 465 | | | |

-continued

| Ex. | (structure with R¹) | K | An⁻ | $\lambda_{max}$ /nm[1] | $\epsilon$ /l/mol cm | $\lambda_{1/2}$-$\lambda_{1/10}$ /nm | $\Delta\lambda$[2] /nm |
|---|---|---|---|---|---|---|---|
| 32 | 3-methyl-5-nitro-2-methyl-thiazolium | 4-methyl-7-methyl-benzoxazine derivative | $ClO_4^-$ | 495 | | | |
| 33 | 2,3-dimethyl-benzothiazolium | 4-(N,N-dimethylamino)toluene | $ClO_4^-$ | 590 | | | |
| 34 | 3-(2-carbamoylethyl)-2-methyl-benzothiazolium | " | $ClO_4^-$ | 593 | | | |
| 35 | 6-methoxy-2,3-dimethyl-benzothiazolium | N,N-diethyl-4-methyl-3-(methylsulfonylamino)aniline | $BF_4^-$ | 586 | 62000 | | |
| 36 | " | N,N-bis(2-cyanoethyl)-4-methylaniline | $BF_4^-$ | 601 | 67750 | | |
| 37 | " | N,N-bis(2-cyanoethyl)-3,4-dimethylaniline | $CH_3SO_3^-$ | 607 | 71480 | | 15 |
| 38 | 3-(2-carbamoylethyl)-6-chloro-2-methyl-benzothiazolium | 2-methyl-5-pyrrolidinyl-3-(phenylsulfonylamino)aniline | $BF_4^-$ | 591 | | | |

[1] in methanol, unless indicated otherwise.
[2] $\Delta\lambda = |\lambda_{\text{methylene chloride}} - \lambda_{\text{methanol}}|$
[3] on the short-wave slope
[4] on the long-wave slope

Example 39

A 4% by weight solution of the dye of Example 27 in 2,2,3,3-tetrafluoropropanol was prepared at room temperature. This solution was applied by means of spin-coating to a pre-grooved polycarbonate substrate. The pre-grooved polycarbonate substrate was produced in the form of a disc by injection-moulding. The dimensions of the disc and the groove structure corresponded to those usually employed for DVD-R's. The disc containing the dye layer as the information carrier was vapour-plated with 100 nm of silver. Then a UV-curable acrylic lacquer was applied by spin-coating and cured using a UV lamp. Using a dynamic recording test setup constructed on an optical bench and consisting of a diode laser ($\lambda$=405 nm) for producing linearly polarized light, a polarization-sensitive beam splitter, a $\lambda$/4-plate and a movably suspended collective lens with a numerical aperture NA of 0.65 (actuator lens), experiments on the recording (writing) and reading of data were carried out. The light reflected from the reflecting layer of the disc was coupled out of the beam path with the aid of the abovementioned polarization-sensitive beam splitter and focussed onto a four-quadrant detector through an astigmatic lens. At a linear velocity of V=2.6 m/s and a recording (writing) power of $P_w$=13.2 mW a signal-to-noise ratio of C/N=42 dB was measured. The recording power was applied as an oscillating pulse sequence, the disc being irradiated alternately for 1 $\mu$s with the abovementioned recording power $P_w$ and for 4 $\mu$s with the reading power $P_r \approx$0.44 mW. The disc was irradiated with this oscillating pulse sequence until it had turned completely a single time. Then the marking produced was read with a reading power $P_r \approx$0.44 mW and the abovementioned signal-to-noise ratio C/N was determined.

Optical data storage media were obtained analogously using the other examples from the above table.

What is claimed is:

1. An optical data storage medium containing a substrate which has optionally already been coated with one or more reflecting layers and onto the surface of which a photorecordable information layer, optionally one or more reflecting layers and optionally a protective layer or an additional substrate or a top layer are applied, which data storage medium can be recorded on and read using blue light, wherein the information layer contains a light-absorbing compound and optionally a binder, wherein at least one diaza hemicyanine dye is used as the light-absorbing compound.

2. The optical data storage medium according to claim 1, wherein the hemicyaine corresponds to the formula (I)

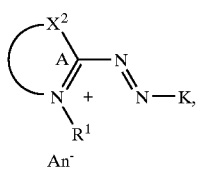

(I)

in which

K represents a radical of the formulae (II) to (IV)

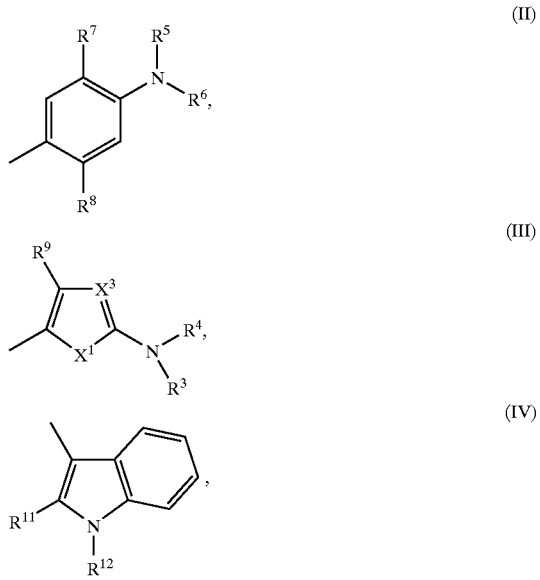

$X^1$ represents O or S, $X^2$ represents O, S, CH or N—$R^2$, $X^3$ represents N, CH or C—CN, $R^1$, $R^2$ and $R^{12}$ independently of one another represent $C_1$- to $C_{16}$-alkyl, $C_3$- to $C_6$-alkenyl, $C_5$- to $C_7$-cycloalkyl or $C_7$- to $C_{16}$-aralkyl, A together with $X^2$ and the C-atom bound there between represents a five-membered aromatic or quasi-aromatic heterocyclic ring which can contain 1 to 4 hetero atoms and/or can be benzo- or naphtho-fused and/or substituted by non-ionic radicals, $R^3$, $R^4$, $R^5$ and $R^6$ independently of one another represent hydrogen, $C_1$- to $C_{16}$-alkyl, $C_4$- to $C_7$-cycloalkyl, $C_7$- to $C_{16}$-aralkyl or a heterocyclic radical or $NR^3R^4$ or $NR^5R^6$ independently of one another represents five- or six-membered saturated ring which is attached via N and can additionally contain an N or O atom and/or be substituted by non-ionic radicals, $R^7$ represents hydrogen, $C_1$- to $C_{16}$-alkyl, $C_1$- to $C_{16}$-alkoxy or halogen or $R^7$ and $R^5$ form a two- or three-membered bridge which can contain an O or N atom and/or be substituted by non-ionic radicals, $R^8$ represents hydrogen, $C_1$- to $C_{16}$-alkyl, $C_1$- to $C_{16}$-alkoxy, halogen, cyano, $C_1$- to $C_4$-alkoxycarbonyl, O—CO—$R^{10}$, NH—CO—$R^{10}$, O—$SO_2$—$R^{10}$ or NH—$SO_2$—$R^{10}$, $R^9$ represents hydrogen, $C_1$- to $C_4$-alkyl or $C_6$- to $C_{10}$-aryl, $R^{10}$ represents hydrogen, $C_1$- to $C_{16}$-alkyl, $C_4$- to $C_7$-cycloalkyl, $C_7$- to $C_{16}$-aralkyl, $C_1$- to $C_{16}$-alkoxy, mono- or bis-$C_1$- to $C_{16}$-alkylamino, $C_7$- to $C_{10}$-aryl, $C_6$- to $C_{10}$-aryloxy, $C_6$- to $C_{16}$-arylamino or a heterocyclic radical, $R^{11}$ represents hydrogen, $C_1$- to $C_4$-alkyl or $C_6$- to $C_{10}$-aryl and An⁻ represents an anion.

3. The optical data storage medium according to claim 2, wherein in the formula (I)

the ring A of the formula

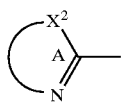
(V)

represents thiazol-2-yl, benzothiazol-2-yl, benzoxazol-2-yl, benzimidazol-2-yl, imidazol-2-yl, pyrazol-3-yl, 1,3,4-triazol-2-yl, 1,3,4-thiadiazol-2-yl, 1,2,4-thiadiazol-5-yl, 2- or 4-pyridyl or 2- or 4-quinolyl, wherein the aforementioned rings can each be substituted by $C_1$- to $C_6$-alkyl, $C_1$- to $C_6$-alkoxy, fluorine, chlorine, bromine, iodine, cyano, nitro, $C_1$- to $C_6$-alkoxycarbonyl, $C_1$- to $C_6$-alkylthio, $C_1$- to $C_6$-acylamino, $C_6$- to $C_{10}$-aryl, $C_6$- to $C_{10}$-aryloxy, $C_6$- to $C_{10}$-arylcarbonylamino, mono- or di-$C_1$- to $C_6$-alkylamino, N—$C_1$- to $C_6$-alkyl-N—$C_6$- to $C_{10}$-arylamino, pyrrolidino, morpholino or piperazino.

4. The optical data storage medium according to claim 2, wherein the diaza hemicyanine corresponds to the formula (I),
in which
the ring A of the formula

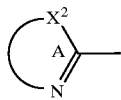
(V)

represents thiazol-2-yl, benzothiazol-2-yl, wherein $X^2$ represents S and the aforementioned radicals can each be substituted by methyl, ethyl, methoxy, ethoxy, chlorine, cyano, methoxycarbonyl or ethoxycarbonyl, or represents 1,3,4-triazolyl or 1,3,4-thiadiazolyl, wherein $X^2$ represents N—$R^2$ or S, respectively, and the aforementioned radicals can each be substituted by methyl, ethyl, phenyl, methoxy, ethoxy, methylthio, ethylthio, amino, anilino, dimethylamino, diethylamino, dipropylamino, dibutylamino, N-methyl-N-cyanethylamino, N-methyl-N-hydroxyethylamino, N-methyl-N-phenylamino, di-(cyanethyl)amino, di-(hydroxyethyl)amino, cyanethylamino, hydroxyethylamino, pyrrolidino, piperidino, morpholino or a radical of the formula

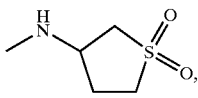

K represents a radical of the formulae (II), (III) or (IV),
$X^1$ represents O or S,
$X^3$ represents N, CH or C—CN.
$R^1$, $R^2$ and $R^{12}$ independently of one another represent methyl, ethyl, propyl, butyl, pentyl, hexyl, benzyl, phenethyl, phenylpropyl, allyl, cyclohexyl, chloroethyl, cyanomethyl, cyanoethyl, cyanopropyl, hydroxyethyl, 2-hydroxypropyl, methoxyethyl or ethoxyethyl,
$R^3$, $R^4$, $R^5$ and $R^6$ independently of one another represent methyl, ethyl, propyl, butyl, pentyl, hexyl, benzyl, phenethyl, phenylpropyl, cyclohexyl, chloroethyl, cyanomethyl, cyanoethyl, cyanopropyl, hydroxyethyl, 2-hydroxypropyl, methoxyethyl, ethoxyethyl, methoxycarbonylethyl, ethoxycarbonylethyl, acetoxyethyl, propionyloxyethyl or a radical of the formula

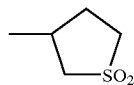

and $R^3$ and $R^5$ can additionally represent hydrogen or $NR^3R^4$ and $NR^5R^6$ independently of one another represent pyrrolidino, piperidino, N-methylpiperazino, N-ethylpiperazino, N-hydroxyethyl-piperazino or morpholino,
$R^7$ represents hydrogen, methyl, methoxy or chlorine or $R^7$; $R^5$ represent a —$(CH_2)_2$—, —$(CH_2)_3$—, —$C(CH_3)$—$CH_2$—$C(CH_3)_2$— or —O—$(CH_2)_2$— bridge,
$R^8$ represents hydrogen, methyl, methoxy or chlorine,
$R^9$ represents hydrogen,
$R^{11}$ represents hydrogen, methyl or phenyl and
An⁻ represents an anion.

5. The optical data storage medium according to claim 1 wherein the diaza hemicyanine corresponds to the formula (VI) to (IX)

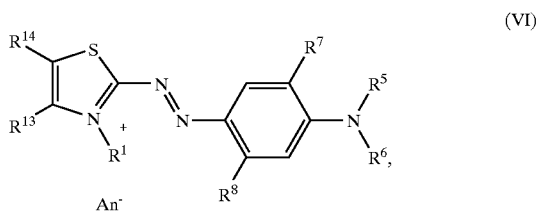
(VI)

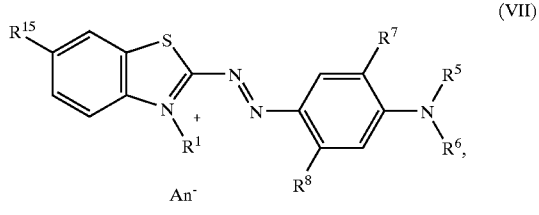
(VII)

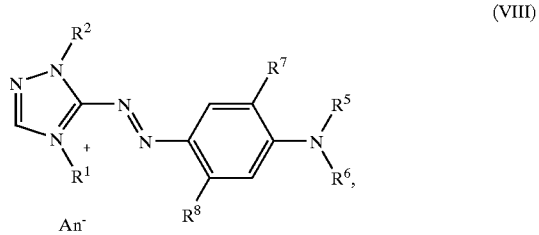
(VIII)

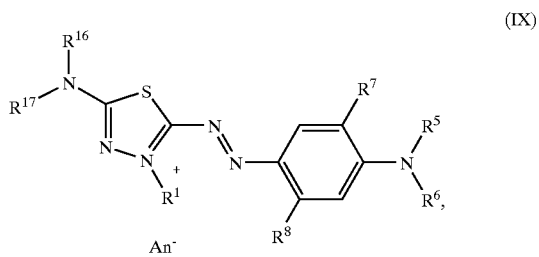
(IX)

in which
$R^1$ and $R^2$ independently of one another represent methyl, ethyl, propyl, butyl, pentyl, hexyl, benzyl, cyclohexyl, chloroethyl, cyanomethyl, cyanoethyl, hydroxyethyl, 2-hydroxypropyl, methoxyethyl, ethoxyethyl or a radical of the formula

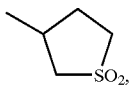

$R^5$ and $R^6$ independently of one another represent methyl, ethyl, propyl, butyl, pentyl, hexyl, benzyl, cyclohexyl, chloroethyl, cyanoethyl, hydroxyethyl, 2-hydroxypropyl, methoxyethyl, ethoxyethyl, methoxycarbonylethyl, ethoxycarbonylethyl or acetoxyethyl or $NR^5R^6$ represents pyrrolidino, piperidino or morpholino, $R^7$ represents hydrogen or $R^7$; $R^5$ represent a —(CH$_2$)$_2$—, —C(CH$_3$)—CH$_2$—C(CH$_3$)$_2$— or —O—(CH$_2$)$_2$— bridge, $R^8$ represents hydrogen, $R^{13}$, $R^{14}$ and $R^{15}$ independently of one another represent hydrogen, methyl, methoxy, chloro, nitro or cyano, $R^{16}$ and $R^{17}$ independently of one another represent methyl, ethyl, propyl, butyl, pentyl, hexyl, benzyl, cyclohexyl, chloroethyl, cyanoethyl, hydroxyethyl, 2-hydroxypropyl, methoxyethyl, ethoxyethyl, methoxycarbonylethyl, ethoxycarbonylethyl, acetoxyethyl or phenyl and $R^{16}$ additionally represents hydrogen or $NR^{16}R^{17}$ represents pyrrolidino, piperidino or morpholino, and An⁻ represents tetrafluoroborate, perchlorate, hexafluorosilicate, hexafluorophosphate, iodide, rhodanide, cyanate, hydroxy acetate, methoxy acetate, lactate, citrate, methane sulphonate, ethane sulphonate, benzene sulphonate, toluene sulphonate, butylbenzene sulphonate, chlorobenzene sulphonate, dodecylbenzene sulphonate or naphthalene sulphonate, wherein all alkyl radicals can be branched.

6. The optical data storage medium according to claim 1 wherein the diaza hemicyanine corresponds to the formula (X) to (XIII)

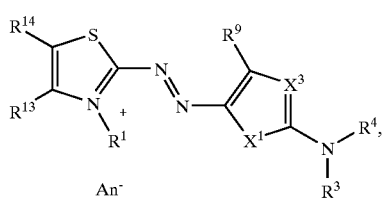
(X)

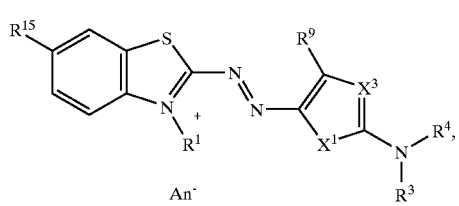
(XI)

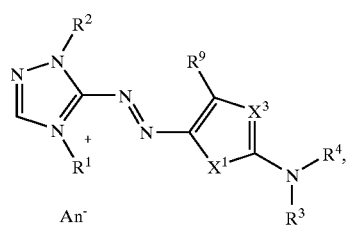
(XII)

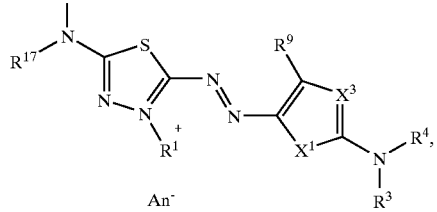
(XIII)

in which $R^1$ and $R^2$ independantly of one another represent methyl, ethyl, propyl, butyl, pentyl, hexyl, benzyl, cyclohexyl, chloroethyl, cyanomethyl, cyanoethyl, hydroxyethyl, 2-hydroxypropyl, methoxyethyl, ethoxyethyl or a radical of the formula

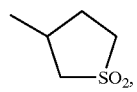

$X^1$ represents O and
$X^3$ represents CH or
$X^1$ represents S and
$X^3$ represents N, CH or C—CN, $R^3$ and $R^4$ independently of one another represent methyl, ethyl, propyl, butyl, pentyl, hexyl, benzyl, cyclohexyl, chloroethyl, cyanoethyl, hydroxyethyl, 2-hydroxypropyl, methoxyethyl, ethoxyethyl, methoxycarbonylethyl, ethoxycarbonylethyl or acetoxyethyl or $NR^3R^4$ represents pyrrolidino, piperidino or morpholino, $R^9$ represents hydrogen, $R^{13}$, $R^{14}$ and $R^{15}$ independently of one another represent hydrogen, methyl, methoxy, cloro, nitro or cyano, $R^{16}$ and $R^{17}$ independently of one another represent methyl, ethyl, propyl, butyl, pentyl, hexyl, benzyl, cyclohexyl, chloroethyl, cyanoethyl, hydroxyethyl, 2-hydroxypropyl, methoxyethyl, ethoxyethyl, methoxycarbonylethyl, ethoxycarbonylethyl, acetoxyethyl or phenyl and $R^{16}$ additionally represents hydrogen or $NR^{16}R^{17}$ represents pyrrolidino, piperidino or morpholino, and An⁻ represents tetrafluoroborate, perchlorate, hexafluorosilicate, hexafluorophosphate, iodide, rhodanide, cyanate, hydroxy acetate, methoxy acetate, lactate, citrate, methane sulphonate, ethane sulphonate, benzene sulphonate, toluene sulphonate, butylbenzene sulphonate, chlorobenzene sulphonate, dodecylbenzene sulphonate or naphthalene sulphonate, wherein all alkyl radicals can be branched.

7. The optical data storage medium according to claim 1 wherein the diaza hemicyanine corresponds to the formula (XIV) to (XVII)

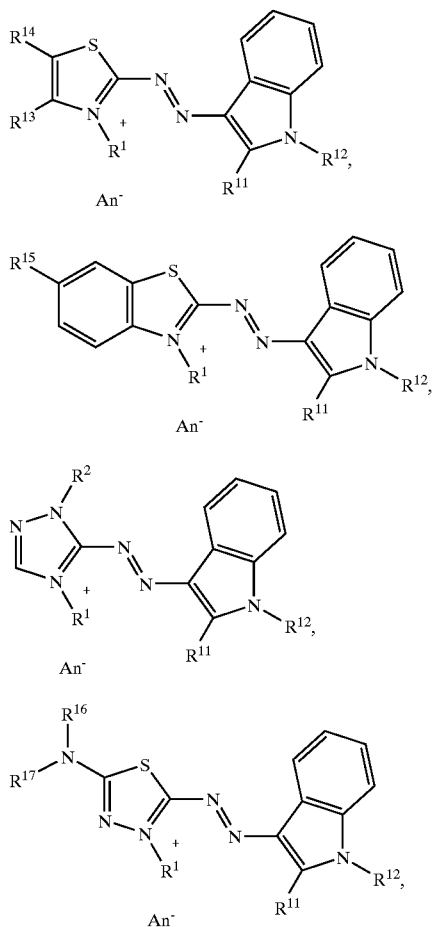

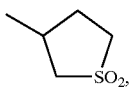

in which
R$^1$, R$^2$ and R$^{12}$ independently of one another represent methyl, ethyl, propyl, butyl, pentyl, hexyl, benzyl, cyclohexyl, chloroethyl, cyanomethyl, cyanoethyl, hydroxyethyl, 2-hydroxypropyl, methoxyethyl, ethoxyethyl or a radical of the formula R$^{13}$, R$^{14}$ and R$^{16}$ independently of one another represent hydrogen, methyl, methoxy, chloro, nitro or cyano,
R$^{16}$ and R$^{17}$ independently of one another represent methyl, ethyl, propyl, butyl, pentyl, hexyl, benzyl, cyclohexyl, chloroethyl, cyanoethyl, hydroxyethyl, 2-hydroxypropyl, methoxyethyl, ethoxyethyl, methoxycarbonylethyl, ethoxycarbonylethyl, acetoxyethyl or phenyl and
R$^{16}$ additionally represents hydrogen or
NR$^{16}$R$^{17}$ represents pyrrolidino, piperidino or morpholino,
R$^{11}$ represents hydrogen, methyl or phenyl and
An$^-$ represents tetrafluoroborate, perchlorate, hexafluorosilicate, hexafluorophosphate, iodide, rhodanide, cyanate, hydroxy acetate, methoxy acetate, lactate, citrate, methane sulphonate, ethane sulphonate, benzene sulphonate, toluene sulphonate, butylbenzene sulphonate, chlorobenzene sulphonate, dodecylbenzene sulphonate or naphthalene sulphonate,
wherein all alkyl radicals can be branched.

8. Diaza hemicyanines corresponding to the formulae (X) to (XIII)

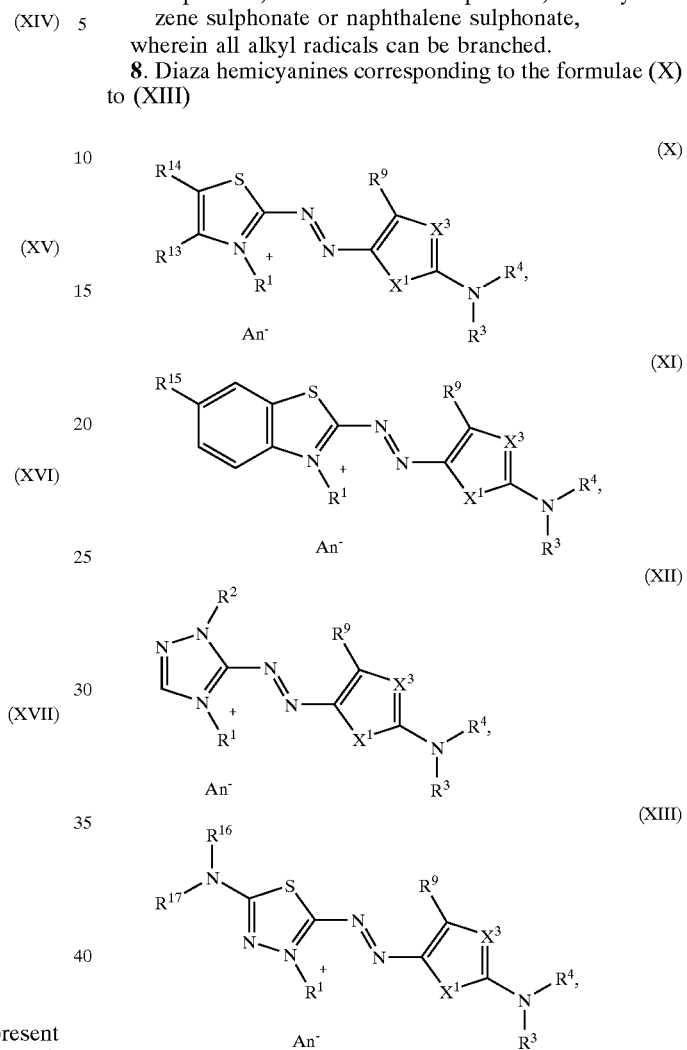

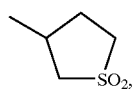

in which
R$^1$ and R$^2$ independently of one another represent methyl, ethyl, propyl, butyl, pentyl, hexyl, benzyl, cyclohexyl, chloroethyl, cyanomethyl, cyanoethyl, hydroxyethyl, 2-hydroxypropyl, methoxyethyl, ethoxyethyl or a radical of the formula X$^1$ represents O and
X$^3$ represents CH or
X$^1$ represents S and
X$^3$ represents CH or C—CN,
R$^3$ and R$^4$ independently of one another represent methyl, ethyl, propyl, butyl, pentyl, hexyl, benzyl, cyclohexyl, chloroethyl, cyanoethyl, hydroxyethyl, 2-hydroxypropyl, methoxyethyl, ethoxyethyl, methoxycarbonylethyl, ethoxycarbonylethyl or acetoxyethyl or NR³R⁴ represents pyrrolidino, piperidino or morpholino, R⁹ represents hydrogen, R¹³, R¹⁴ and R¹⁵ independently of one another represent hydrogen, methyl, methoxy, cloro, nitro or cyano, R¹⁶ and R¹⁷ independently of one another represent methyl, ethyl, propyl, butyl, pentyl, hexyl, benzyl, cyclohexyl, chloroethyl, cyanoethyl, hydroxyethyl, 2-hydroxypropyl, methoxyethyl, ethoxyethyl, methoxycarbonylethyl, ethoxycarbonylethyl, acetoxyethyl or phenyl and R¹⁶ additionally represents hydrogen or NR¹⁶R¹⁷ represents pyrrolidino, piperidino or morpholino, and An⁻ represents tetrafluoroborate, perchlorate, hexafluorosilicate, hexafluorophosphate, iodide, rhodanide, cyanate, hydroxy acetate, methoxy acetate, lactate, citrate, methane sulphonate, ethane sulphonate, benzene sulphonate, toluene sulphonate, butylbenzene sulphonate, chlorobenzene sulphonate, dodecylbenzene sulphonate or naphthalene sulphonate, wherein all alkyl radicals are optionally branched.

9. A process for manufacturing recordable optical data storage media comprising applying diaza hemicyanines in its information layer, wherein the hemicyanines have an absorption maximum $\lambda_{max2}$ in the range from 420 to 650 nm.

10. A process for manufacturing recordable optical data storage media comprising applying diaza hemicyanines in its information layer, wherein the data storage media are recorded on and read with a blue laser light.

11. A process for producing the optical data storage media according to claim 1, wherein a substrate, which has optionally already been coated with a reflecting layer, is coated with the diaza hemicyanines, optionally in combination with suitable binders and additives and optionally suitable solvents, and is optionally provided with a reflecting layer, additional intermediate layers and optionally a protective layer or an additional substrate or a top layer.

12. Optical data storage media according to claim 1 which have been recorded on using blue light.

13. An optical data storage medium containing a substrate which has optionally already been coated with one or more reflecting layers and onto the surface of which a photorecordable information layer, optionally one or more reflecting layers and optionally a protective layer or an additional substrate or a top layer are applied, which data storage medium can be recorded on and read using red light, wherein the information layer contains a light-absorbing compound and optionally a binder, wherein at least one diaza hemicyanine dye is used as the light-absorbing compound which corresponds to the formula (I)

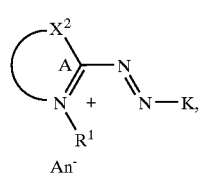
(I)

in which

K represents a radical of the formula (III)

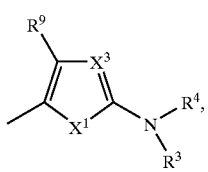
(III)

X¹ represents O or S,

X² represents O, S, CH or N—R²,

X³ represents N, CH or C—CN,

R¹, R² and R¹² independently of one another represent C₁- to C₁₆-alkyl, C₃- to C₆-alkenyl, C₅- to C₇-cycloalkyl or C₇- to C₁₆-aralkyl, A together with X² and the C-atom bound therebetween represents a five-membered aromatic or quasi-aromatic heterocyclic ring which can contain 1 to 4 hetero atoms and/or can be benzo- or naphtho-fused and/or substituted by non-ionic radicals, R³ and R⁴ independently of one another represent hydrogen, C₁- to C₁₆-alkyl, C₄- to C₇-cycloalkyl, C₇- to C₁₆-aralkyl or a heterocyclic radical or NR³R⁴ represent a five- or six-membered saturated ring which is attached via N and can additionally contain an N or O atom and/or be substituted by non-ionic radicals, R⁹ represents hydrogen, C₁- to C₄-alkyl or C₆- to C₁₀-aryl, An⁻ represents an anion.

14. The optical data storage medium according to claim 13, wherein in the formula (I), in which the ring A of the formula

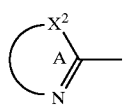
(V)

represents thiazol-2-yl, benzothiazol-2-yl, benzoxazol-2-yl, benzimidazol-2-yl, imidazol-2-yl, pyrazol-3-yl, 1,3,4-triazol-2-yl, 1,3,4-thiadiazol-2-yl, 1,2,4-thiadiazol-5-yl, 2- or 4-pyridyl or 2- or 4-quinolyl, wherein the aforementioned rings can each be substituted by C₁- to C₆-alkyl, C₁- to C₆-alkoxy, fluorine, chlorine, bromine, iodine, cyano, nitro, C₁- to C₆-alkoxycarbonyl, C₁-to C₆-alkylthio, C₁- to C₆-acylamino, C₆- to C₁₀-aryl, C₆- to C₁₀-aryloxy, C₆- to C₁₀-arylcarbonylamino, mono- or di-C₁- to C₆-alkylamino, N—C₁- to C₆-alkyl-N—C₆- to C₁₀-arylamino, pyrrolidino, morpholino or piperazino.

15. The optical data storage medium according to claim 13, wherein the diaza hemicyanine corresponds to the formula (I), in which the ring A of the formula

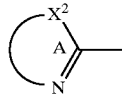
(V)

represents thiazol-2-yl, benzothiazol-2-yl, wherein X² represents S and the aforementioned radicals can each be substituted by methyl, ethyl, methoxy, ethoxy, chlorine, cyano, methoxycarbonyl or ethoxycarbonyl, or represents 1,3,4-triazolyl or 1,3,4-thiadiazolyl, wherein $X^2$ represents N—$R^2$ or S, respectively, and the aforementioned radicals can each be substituted by methyl, ethyl, phenyl, methoxy, ethoxy, methylthio, ethylthio, amino, anilino, dimethylamino, diethylamino, dipropylamino, dibutylamino, N-methyl-N-cyanethylamino, N-methyl-N-hydroxyethylamino, N-methyl-N-phenylamino, di-(cyanethyl)amino, di-(hydroxyethyl)amino, cyanethylamino, hydroxyethylamino, pyrrolidino, piperidino, morpholino or a radical of the formula

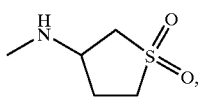

K represents a radical of the formulae (II), (III) or (IV), $X^1$ represents O or S, $X^3$ represents N, CH or C—CN, $R^1$ and $R^2$ independently of one another represent methyl, ethyl, propyl, butyl, pentyl, hexyl, benzyl, phenethyl, phenylpropyl, allyl, cyclohexyl, chloroethyl, cyanomethyl, cyanoethyl, cyanopropyl, hydroxyethyl, 2-hydroxypropyl, methoxyethyl or ethoxyethyl, $R^3$ and $R^4$ independently of one another represent methyl, ethyl, propyl, butyl, pentyl, hexyl, benzyl, phenethyl, phenylpropyl, cyclohexyl, chloroethyl, cyanomethyl, cyanoethyl, cyanopropyl, hydroxyethyl, 2-hydroxypropyl, methoxyethyl, ethoxyethyl, methoxycarbonylethyl, ethoxycarbonylethyl, acetoxyethyl, propionyloxyethyl or a radical of the formula

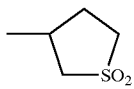

and $R^3$ and $R^5$ can additionally represent hydrogen or $NR^3R^4$ represent pyrrolidino, piperidino, N-methylpiperazino, N-ethylpiperazino, N-hydroxyethylpiperazino or morpholino.

$R^9$ represents hydrogen,

An⁻ represents an anion.

16. The optical data storage medium according to claim 13, wherein the diaza hemicyanine corresponds to the formula (X) to (XIII)

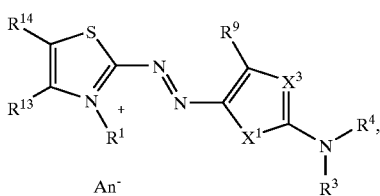

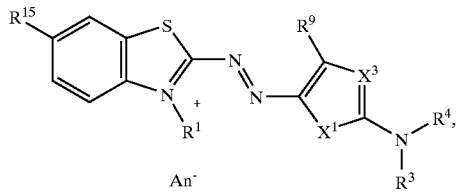

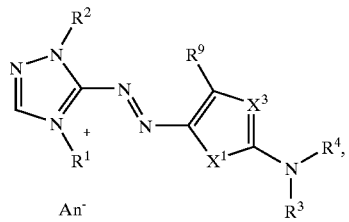

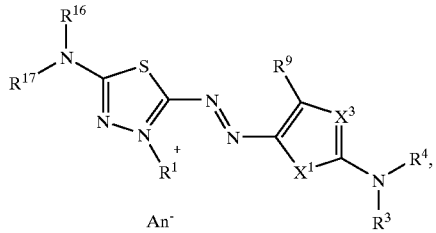

in which $R^1$ and $R^2$ independantly of one another represent methyl, ethyl, propyl, butyl, pentyl, hexyl, benzyl, cyclohexyl, chloroethyl, cyanomethyl, cyanoethyl, hydroxyethyl, 2-hydroxypropyl, methoxyethyl, ethoxyethyl or a radical of the formula

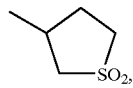

$X^1$ represents O and $X^3$ represents CH or $X^1$ represents S and $X^3$ represents N, CH or C—CN, $R^3$ and $R^4$ independently of one another represent methyl, ethyl, propyl, butyl, pentyl, hexyl, benzyl, cyclohexyl, chloroethyl, cyanoethyl, hydroxyethyl, 2-hydroxypropyl, methoxyethyl, ethoxyethyl, methoxycarbonylethyl, ethoxycarbonylethyl or acetoxyethyl or $NR^3R^4$ represents pyrrolidino, piperidino or morpholino, $R^9$ represents hydrogen, $R^{13}$, $R^{14}$ and $R^{15}$ independently of one another represent hydrogen, methyl, methoxy, cloro, nitro or cyano, $R^{16}$ and $R^{17}$ independently of one another represent methyl, ethyl, propyl, butyl, pentyl, hexyl, benzyl, cyclohexyl, chloroethyl, cyanoethyl, hydroxyethyl, 2-hydroxypropyl, methoxyethyl, ethoxyethyl, methoxycarbonylethyl, ethoxycarbonylethyl, acetoxyethyl or phenyl and $R^{16}$ additionally represents hydrogen or $NR^{16}R^{17}$ represents pyrrolidino, piperidino or morpholino, and An⁻ represents tetrafluoroborate, perchlorate, hexafluorosilicate, hexafluorophosphate, iodide, rhodanide, cyanate, hydroxy acetate, methoxy acetate, lactate, citrate, methane sulphonate, ethane sulphonate, benzene sulphonate, toluene sulphonate, butylbenzene sulphonate, chlorobenzene sulphonate, dodecylbenzene sulphonate or naphthalene sulphonate, wherein all alkyl radicals can be branched.

17. A process for manufacturing recordable optical data storage media according to claim 13 applying diaza hemicyanines in the information layer, wherein the data storage mediaare recorded on and read with a red laser light.

18. A process for producing the optical data storage media according to claim 13, wherein a substrate, which has optionally already been coated with a reflecting layer, is coated with the diaza hemicyanines, optionally in combination with suitable binders and additives and optionally suitable solvents, and is optionally provided with a reflecting layer, additional intermediate layers and optionally a protective layer or an additional substrate or a top layer.

19. Optical data storage media according to claim 13 which have been recorded on using red light.

* * * * *